United States Patent
Bjornson et al.

(10) Patent No.: US 6,638,501 B1
(45) Date of Patent: *Oct. 28, 2003

(54) USE OF MULTIPOTENT NEURAL STEM CELL PROGENY TO AUGMENT NON-NEURAL TISSUES

(75) Inventors: Christopher R. Bjornson, Calgary (CA); Rod L. Rietze, Calgary (CA); Brent A. Reynolds, Saltspring (CA); Angelo L. Vescovi, Milan (IT)

(73) Assignee: Neurospheres Holdings Ltd., Alberta (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/100,296

(22) Filed: Jun. 19, 1998

Related U.S. Application Data

(60) Provisional application No. 60/060,289, filed on Sep. 29, 1997.

(51) Int. Cl.$^7$ .................... A01K 65/00; A01N 65/00; A01N 63/00
(52) U.S. Cl. ............... 424/93.1; 435/1.1; 424/93.7; 424/93.21
(58) Field of Search ............... 435/1.1, 463, 455, 435/325; 424/93.1, 93.2, 93.21, 93.7

(56) References Cited

U.S. PATENT DOCUMENTS

| | | | |
|---|---|---|---|
| 5,550,050 A | 8/1996 | Holland et al. | 435/240.2 |
| 5,650,135 A | 7/1997 | Contag et al. | 424/9.1 |
| 5,750,376 A | 5/1998 | Weiss et al. | 435/69.52 |
| 6,093,531 A * | 7/2000 | Bjornson et al. | 435/1.1 |

FOREIGN PATENT DOCUMENTS

WO WO93/01275 1/1993

OTHER PUBLICATIONS

Holyoake TL et al. Exp Hematology 27:1418–1427, 1999.*
Clarke DL et al. Science 288:1660–1663, 2000).*
Gage FH. Science 287:1433–1438, 2000.*
Bjornson CRR et al. Science 283:534–537, 1999.*
Amos, T.A.S., et al., "Source of Human Hematopoietic Stem Cells for Transplantation—A Review", *Cell Trans.*, 4(6):547–569 (1995).
Bensinger, William, et al., "Factors That Influence Collection and Engraftment of Autologous Peripheral–Blood Stem Cells", *J. Clin. Oncol.*, 13(10):2547–2555 (Oct. 1995).
Chalfie, Martin, et al., "Green Fluorescent Protein as a Marker for Gene Expression", *Sci.*, 263:802–805 (Feb. 1994).
Ferrari, Giuliana, et al., "Muscle Regeneration by Bone Marrow–Derived Myogenic Progenitors", *Sci.*, 279:1528–1530 (Mar. 1998).
Green, Jeremy B.A., et al., "Roads to Neuralness: Embryonic Neural Induction as Derepression of a Default State", *Cell*, 77:317–320 (May 1994).
Hammang, J.P., et al., "Myelination Following Transplantation of EGF–Responsive Neural Stem Cells into a Myelin–Deficient Environment", *Exper. Neurol*, 147:84–95 (1997).
Hemmati–Brivanlou, Ali, et al., "Vertebrate Enmbryonic Cells Will Become Nerve Cells Unless Told Otherwise", *Cell*, 88:13–17 (Jan. 1997).
Keller, Gordon M., "In vitro differentiation of embryonic stem cells", *Cell Biol.*, 7:862–869 (1995).
Kenyon, Norma S., "Emerging Applications of Hematopoietic Stem Cell Transplantation in the Treatment of Insulin Dependent Diabetes", *IBC on Hematopoietic Stem Cells*, 4:45 (Jun. 1997) (Abstract).
Lu, Li, et al., "Stem cells from bone marrow, umbilical cord blood and peripheral blood for clinical application: current status and future application", *Oncol./Hematol.*, 22:61–78 (1996).
Lund–Hansen, T., et al., "A quantitative cytochemical assay of β–galactosidase in single cultured human skin fibroblasts", *Histochem.*, 81(4):321–330 (1984).
Motluk, Alison, "Natural born fathers", *New Sci.*, pp. 38–41 (Dec. 1998).
Nakano, Toru, et al., "Generation of Lymphohematopoietic Cells from Embryonic Stem Cells in Culture", *Sci.*, 265:1098–1101 (Aug. 1994).
Potten, C.S., et al., "Stem cells: attributes, cycles, spirals, pitfalls and uncertainties. Lessons for and from the Crypt", *Dev.*, 110:1001–1020 (1990).
Tricot, Guido, et al., "Peripheral Blood Stem Cell Transplants for Multiple Myeloma: Identification of Favorable Variables for Rapid Engraftment in 225 Patients", *Blood*, 85(2):588–596 (Jan. 1995).
Wobus, Anna M., et al., "Pluripotent mouse embryonic stem cells are able to differentiate into cardiomyocytes expressing chronotropic responses to adrenergic and cholinergic agents and $Ca^{2+}$ channel blockers", *Differentiation*, 48:173–182 (1991).

* cited by examiner

Primary Examiner—Ram R. Shukla
(74) Attorney, Agent, or Firm—Ivor R. Elrifi, Esq.; Christina V. Karnakis, Esq.; Mintz, Levin, Cohn, Ferris, Glovsky and Popeo, P.C.

(57) ABSTRACT

Multipotent neural stem cell (MNSC) progeny are transplanted into a recipient wherein they augment host tissue. The stem cells have a universal lineage potential and are capable of producing progeny that, in response to appropriate environmental signals, can differentiate into a variety of differentiated cell types, and not just neural lineages. MNSCs can be proliferated ex vivo to provide an unlimited supply of stem cells and stem cell progeny which give rise to the differentiated cell types of various tissues. The stem cells are readily amenable to genetic modification, if desired. They also have the advantage that they can be obtained from autologous adult human tissue and thus overcome prior art problems of transplant rejections.

1 Claim, 9 Drawing Sheets

USE OF MULTIPOTENT NEURAL STEM CELL PROGENY TO AUGMENT NON-NEURAL TISSUES

RELATED APPLICATIONS

The present application is related to U.S. application Ser. No. 09/100,679, now U.S. Pat. No. 6,093,531, entitled "Generation of Hematopoietic Cells from Multipotent Neural Stem Cells", which was filed on Jun. 19, 1998, which claims the benefit of U.S. Provisional Application Ser. No. 60/060,289.

BACKGROUND OF THE INVENTION

Cell transplantation is increasingly becoming a therapy of choice for a variety of cell-based disorders ranging from sickle cell anemia and diabetes to Parkinson's disease. For example, cell lines may be transplanted to deliver a biologically active agent such as insulin, for the treatment of diabetes; parathyroid hormone, for treatment of hypoparathyroidism; erythropoietin, for treatment of anemia; and gamma-amino-butyric acid, for treatment of epilepsy. The cells may naturally secrete the biologically active molecule, or be genetically modified to do so. There are several obstacles that prevent cell transplantation therapy from realizing its full potential. For example, obtaining quantities of cells suitable for transplantation is often a problem. Cell lines transformed with oncogenes can pose a risk of unwanted cell migration, unrestricted proliferation, and possibly tumor formation. Transplant rejection is also a potential problem. These problems have been addressed by encapsulating the transplanted cells in immunoisolatory vehicles which retain the cells at a desired location within the transplant recipient, where the cells secrete the biologically active substances. The immunoisolatory vehicle prevents unwanted cell migration, possible tumor formation, and reduces the possibility of transplant rejection. Methods of transplanting encapsulated cells are disclosed in U.S. Pat. No. 5,550,050.

For some cell-based disorders, it is necessary for the transplanted cells to become integrated with the host tissue being treated. In these cases, encapsulation methods cannot be used. Thus, it is important that the transplanted cells are human leukocyte antigen (HLA) matched to the patient's tissue to reduce the likelihood of transplant rejection. Hematopoietic stem cell transplantation, is an example of a therapy where donor cells become integrated with the patient's own tissue. It is an effective therapy for a number of diseases, such as sickle cell anemia, aplastic anemia, and a variety of immunodeficiency disorders, including those which result from treatments for other disorders such as chemo- and radiotherapy treatment for cancer (reviewed in Amos and Gordon, *Cell Transplantation* 4(6):547–569 (1995)). Hematopoietic stem cells, are present in adult bone marrow and blood (in smaller numbers), and are capable of giving rise to all of the cells of the hematopoietic cell lineage. Fetal sources of hematopoietic stem cells in umbilical cord blood and liver, have also been reported. Lu et al., *Critical Rev. in Oncol./Hemataol.* 22:61–78 (1996).

Certain neurological disorders treated by cell transplantation, also require that the cells become integrated with the host tissue. For example, in the treatment of myelin deficiencies, it is necessary for the transplanted cells to reform the insulating cellular sheaths around the axons of demyelinated neurons. Animal models of myelin deficiencies have shown promising results from the transplantation of undifferentiated neural stem cell progeny into demyelinated regions of the central nervous system. Hammang et al., *Experimental Neurology* 147:84–95 (1997).

Several tissues in the body contain stem cells. The primary role of stem cells in adults is to replace cells which have been lost by natural cell death, injury or disease. Stem cells have been defined as "undifferentiated cells capable of a) proliferation, b) self-maintenance, c) the production of a large number of differentiated, functional progeny, d) regenerating tissue after injury, and e) a flexibility in the use of these options". Potten and Loeffler, *Development*, Vol. 110, ¶. 1001–1020 (1990). Stem cells isolated from the early embryonic blastula, i.e. prior to gastrulation, can produce cell types of all different lineages (for review see Keller, G. M. *Curr. Opin. Cell Biol.* 7:862–869 (1995)). More recently, it has been hypothesized that neural tissue is likely to be the default state for all cells during early embryonic development. Green, *Cell* 77:317–320 (1994); Hemmati-Brivanlou & Melton, *Cell* 88:13–17 (1997). However, in the adult, it is generally believed stem cells present in a specific tissue are restricted to produce cell types of that tissue. For example, hematopoietic stem cells derived from adult bone marrow give rise to progeny of the blood, immune system, and myogenic precursors, but have not been reported to give rise to other tissue types. Ferrari et al. *Science* 279:1528–1530 (1998). Similarly, adult neural stem cells obtained from neural tissue have only been reported to give rise to neural specific cell types.

In addition to the treatment of various cell-based diseases and disorders, cell transplantation could also be potentially useful for treating injuries and/or strengthening, or otherwise, augmenting various tissues such as, skin, heart muscle, and bone. However, lack of availability of sufficient quantities of compatible, healthy cells of the required phenotype, which can become integrated with the desired tissue, prevents cell transplantation therapies from reaching their full potential. For example, in the treatment of bone marrow diseases, it is difficult to find well-matched donors who are willing to be subjected to the painful and time-consuming bone marrow donation process.

A reliable source of cells that can be used for transplantation, with reduced risk of rejection, to replace or augment cells in a variety of tissues is needed.

SUMMARY OF THE INVENTION

It is an object of the invention to provide a source of stem cells that can be used to augment any type of mammalian tissue including, but not limited to, bone marrow, liver, thymus, spleen, pancreas, heart muscle, lung, skin, skeletal muscle, smooth muscle, gonadal, intestinal, central nervous system (CNS), and lymph tissue. It is also an object of the invention that the stem cells be obtainable from autologous, allogeneic, or xenogeneic tissue, and readily proliferated ex vivo to generate a sufficient number of cells for tissue augmentation.

These objects are achieved by providing methods for augmenting one or more tissues of a mammal by administering multipotent neural stem cell (MNSC) progeny to the mammal and allowing the MNSC progeny to integrate with the tissue. The MNSC progeny can be administered to the mammal by any suitable method. For example, the cells can be administered systemically, where they migrate to tissues requiring augmentation, they can be applied close to the periphery of the tissue to be augmented, or injected or applied directly to the tissue to be augmented. In the treatment or augmentation of CNS tissue, MNSC progeny can be administered outside the CNS, and migrate to the CNS and differentiate into CNS cells.

Methods for generating differentiated non-neural mammalian cells from MNSC progeny are also provided which comprise placing the multipotent neural stem cell progeny in an environment that induces them to produce the differentiated non-neural cells.

DESCRIPTION OF THE DRAWINGS

The file of this patent contains at least one drawing executed in color. Copies of this patent with color drawings will be provided by the Patent and Trademark Office upon request and payment of the necessary fee.

FIG. 1C shows a tissue section of a spleen harvested from a test mouse. The presence of β-gal expressing cells, and demonstrates that some of the administered MNSC progeny integrated with the tissue of the spleen.

FIG. 1F shows tissue from a test mouse following X-gal histochemistry and indicates that some of the administered MNSC progeny integrated with the tissue of the thymus.

FIG. 2A (Mag. 20×) shows tissue from an EBSS negative control. FIG. 2B shows a tissue section of a portion of the small intestine harvested from a test mouse (Mag. 20×) following X-Gal histochemistry and indicates that some of the administered MNSC progeny integrated with the small intestine tissue. FIG. 2C shows a higher magnification (63×) of another region of the small intestine tissue of the same test mouse as shown in FIG. 2B.

FIG. 2E shows tissue from a test mouse following X-gal histochemistry and indicates that some of the administered MNSC progeny integrated with the lymphatic tissue.

FIGS. 3C and 3D show tissue sections of different regions of testes harvested from a test mouse (Mag. 63×) following X-gal histochemistry and indicates that some of the administered MNSC progeny integrated with the tissue of the testes.

FIG. 3G shows a tissue section of a portion of brain harvested from a test mouse (Mag. 20×) following X-gal histochemistry and indicates that some of the administered MNSC progeny integrated with the tissue of the brain. FIG. 3H is a higher magnification (63×) of the same brain region shown in FIG. 3G.

FIGS. 4B, 4D, 4F, 4H, 4J, and 4L are higher magnification photos (63×) of the same region of tissue as shown in FIGS. 4A, 4C, 4E, 4G, 4I, and 4K, respectively. Positive controls are shown in FIGS. 4A and 4B. Negative controls are shown in FIGS. 4C and 4D. Tissue sections from various regions of the brain harvested from test mice are shown in FIGS. 4E, 4G, 4I, and 4K (Mag. 20×), and FIGS. 4F, 4H, 4J, and 4L (Mag. 63×). The arrows point to cells which indicate that some of the peripherally administered MNSC progeny integrated with tissue of the central nervous system following X-gal histochemistry.

DETAILED DESCRIPTION OF THE INVENTION

Figure 1A:
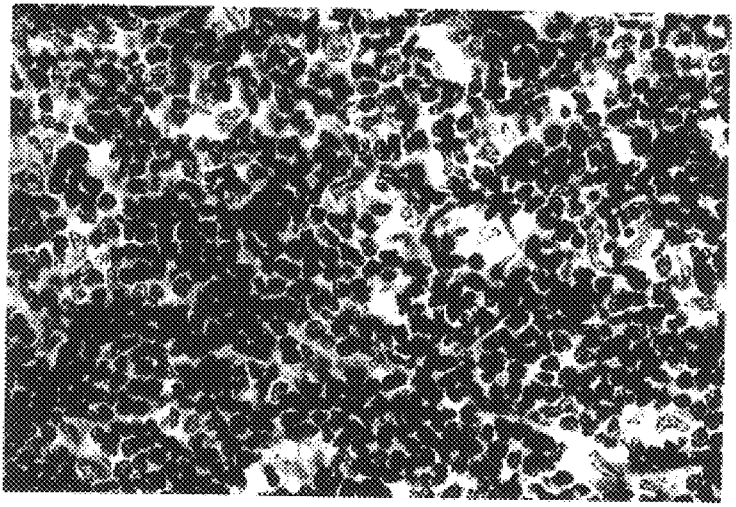
FIGS. 1A–1C show tissue sections (10 µm) of mouse spleens which were assayed for the presence of beta-galactosidase (β-gal) labeled cells using X-gal histochemistry (Mag. 63×). The few Balb/C mice which had been irradiated and survived after being administered only Earl's Buffered Saline Solution systemically, were used as negative controls (hereinafter referred to as "EBSS negative control") (FIG. 1A). Non-irradiated ROSA mice, which are genetically labeled to express β-gal, were used as positive controls (hereinafter referred to as "ROSA positive control") (FIG. 1B). The experimental animals were Balb/c mice that survived at least 6 months following irradiation and systemic injection of β-Gal labeled MNSC progeny. These mice are referred to herein as "test mice").

The contents of U.S. application Ser. No. 09/100,679, now U.S. Pat. No. 6,093,531, entitled "Generation of Hematopoietic Cells from Multipotent Neural Stem Cells, which was filed on Jun. 19, 1998, and which is a continuation-in-part of provisional application no. 60/060,289, filed Sep. 29, 1997, are incorporated herein by reference. That application discloses the significant discovery that multipotent neural stem cells (MNSCs) which can be obtained from non-tumorous embryonic and adult neural tissue, and continuously proliferated ex vivo (as described in WO 93/01275 and in U.S. Pat. No. 5,750,376) without being transformed with oncogenes, are capable of producing progeny that differentiate into cells of the hematopoietic system. Specifically, that application discloses that labeled, undifferentiated MNSC progeny were systemically administered to animals that had their hematopoietic systems severely compromised by irradiation. The majority of irradiated animals that were administered the MNSC cell progeny survived for prolonged periods (greater than six months). The injected MNSC cell progeny gave rise to cells that were capable of repopulating the hematopoietic system back to levels seen before irradiation. These newly-generated cell types included, but were not limited to, CD3e, CD4, CD8, CD11b and CD19 cells. In sharp contrast, the majority of control animals that were irradiated, but did not receive an injection of MNSCs, died within a short time period (within approximately one month).

The present application concerns the further discovery that MNSC progeny can be influenced by environmental signals to produce progeny that differentiate into tissue-appropriate cells, which are not restricted to neural and blood lineages. A multipotent neural stem cell is an undifferentiated cell that can be found in neural tissue of embryonic, fetal, neonatal, juvenile and adult mammals, and may exist in non-neural tissues as well. It can be induced to proliferate ex vivo by the presence of one or more growth factors, including epidermal and/or fibroblast growth factors, to give rise to undifferentiated progeny which includes daughter MNSCs and progenitor cells. The progenitor cells can be induced to differentiate ex vivo or in vivo into neurons, astrocytes, and oligodendrocytes. Methods of continuously proliferating MNSCs ex vivo and inducing the neural differentiation of MNSC progeny are disclosed in U.S. Pat. No. 5,750,376.

Applicants have discovered that by selecting or altering the environment in which MNSCs and their undifferentiated progeny are placed, the ultimate fate of the neural stem cell progeny into either neural (ectodermal) or non-neural (ectodermal, endodermal and mesodermal) cells can be directed. When administered systemically, MNSC progeny relocate to numerous regions where non-neural stem cells are normally found including, for example, tissues where there is normally high cell turnover. Thus, it is believed that the multipotent neural stem cell is a pluripotent stem cell, and perhaps even an omnipotent stem cell, that, depending on the environment in which it is placed, can give rise to differentiated cells of any tissue type, in addition to neural and blood tissue.

When reference is made herein to the environment in which MNSC progeny are placed, the common meaning of the term "environment" is intended. Thus, the term refers to the combination of external or extrinsic physical conditions that affect and influence the growth and development of multipotent neural stem cells and/or their progeny. The environment can be ex vivo or in vivo. For example, Example 7 of U.S. Pat. No. 5,750,376, describes various culture conditions that induce multipotent neural stem cell progeny to give rise to neurons, astrocytes and oligodendrocytes. Hence, these culture conditions are ex vivo environments that induce multipotent neural stem cells and/or their progeny to give rise to differentiated neural cells. An example of an in vivo environment that affects and influences the growth and development of multipotent neural stem cells and/or their progeny is provided in Example 15 of U.S. Pat. No. 5,750,376, where MNSC progeny placed near an axon of a myelin-deficient rat gave rise to myelin (i.e. oligodendrocytes were generated).

Because of the universal potential of MNSCs, MNSCs and their progeny can be administered to a recipient mammal to augment one or more selected tissues of the mammal. By the term "augmented", it is meant that the transplanted neural stem cells and/or neural stem cell progeny provide a needed or added function to recipient tissue. Usually, it is preferred that the augmentation includes integration of the transplanted cells or their progeny with the recipient tissue. One type of tissue augmentation that the MNSC progeny may achieve, is a strengthening of, or otherwise increase in, the mass of a particular tissue. Another way in which neural stem cell progeny can augment tissue is by secreting biologically active agents the tissue needs for normal functioning or for treatment of disease. Transplantation of MNSC progeny may also be used to repair damaged tissues. It can also be used to augment normal tissue whereby the transplanted MNSC progeny provide an added function to the treated tissue to render it supra-normal, for example by endowing the tissue with an ability that is not normally present in the tissue. Undifferentiated transplanted MNSC progeny can augment tissue by serving as a reserve source of cells, which proliferate and/or differentiate as needed in response to environmental signals that may be triggered by injury, aging, or other stimulus. Thus, the cells that augment the transplanted tissue may be undifferentiated and/or differentiated cells. They may comprise the cells that were initially transplanted to the recipient mammal, and/or may comprise the differentiated or undifferentiated progeny of the cells that were initially transplanted.

When reference is made to administering or transplanting MNSC progeny to augment a selected tissue, the terms "administer", "administering", "transplant" and "transplanting" are intended to encompass any suitable method of causing the MNSC progeny to come in contact with the selected tissue. The MNSC progeny can be administered directly to the tissue being augmented or near the tissue being augmented (where the transplanted cells may migrate to and become integrated with the selected tissue). MNSC progeny can also be administered to one or more sites distant from the tissue being augmented, for example, by systemic, subcutaneous, or intraperitoneal administration. As shown in the Figures, systemic administration of MNSC progeny allows the transplanted cells to integrate with a variety of tissues.

Figure 4A:
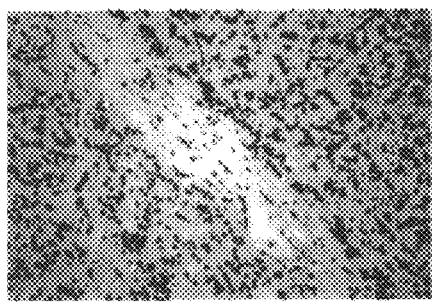
FIGS. 4A–4L show tissue sections (10 µm) of mouse central nervous tissue (brain) which were assayed for the presence of β-gal.
Figure 4B:
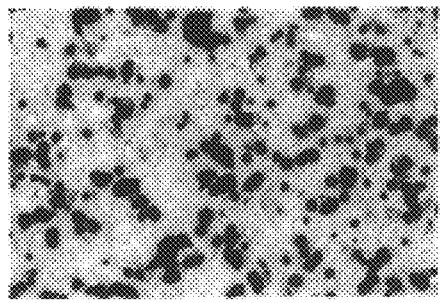
Figure 4C:
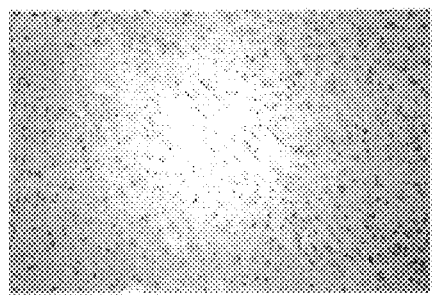
Figure 4D:
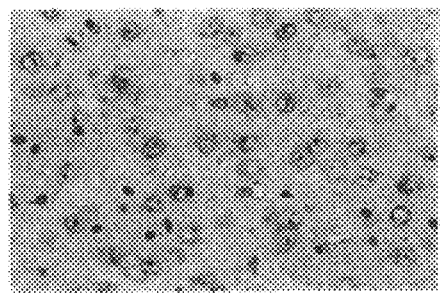
Figure 4E:
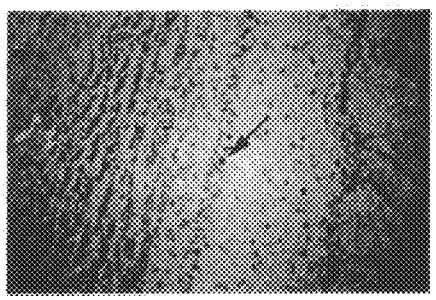
Figure 4F:
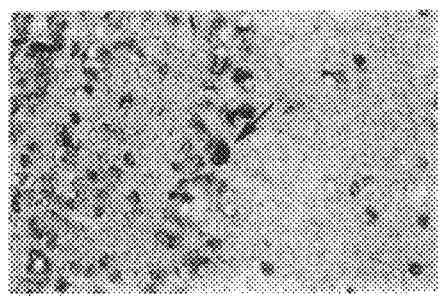
Figure 4G:
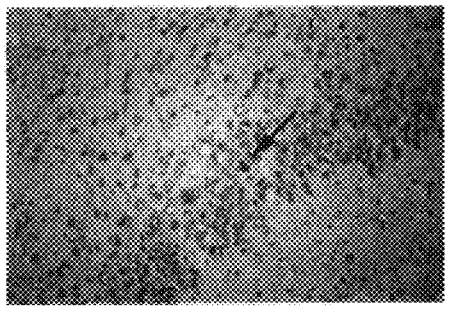
Figure 4H:
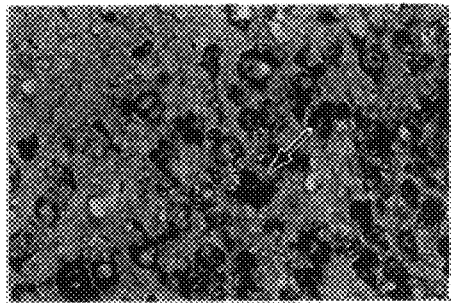
Figure 4I:
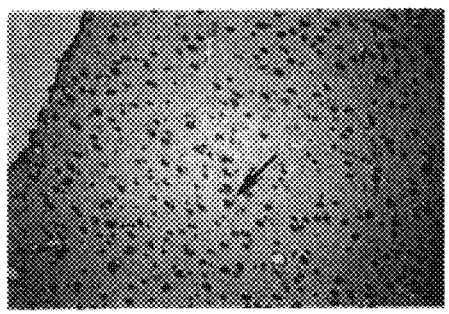
Figure 4J:
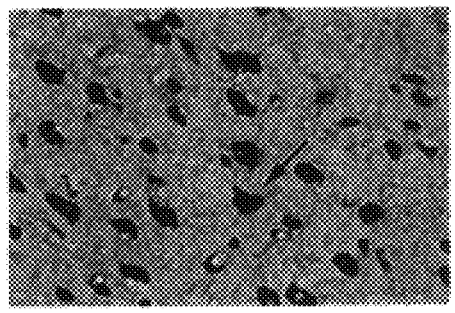
Figure 4K:
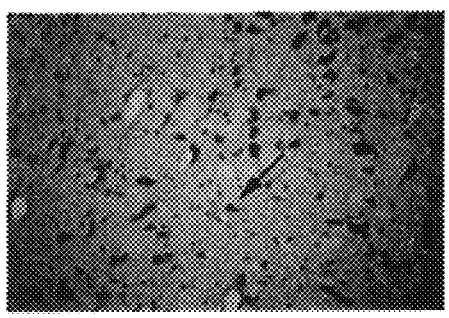
Figure 4L:
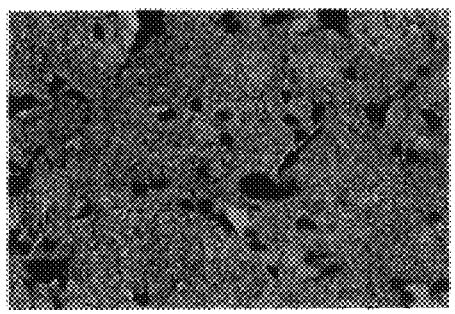

Any mammalian tissue can be augmented using MNSC progeny including, but not limited to blood, bone marrow, liver, thymus, spleen, pancreas, heart muscle, lung, skin (pilated and nonpilated), skeletal muscle, smooth muscle, gonadal, intestinal, central nervous system, bone, peripheral nervous system and lymph tissue. For example, systemically administered MNSC progeny can migrate to various regions of the brain, demonstrating the ability to bypass the blood-brain barrier (see Example 1, and FIGS. 4E–4L) and incorporate with the CNS. Therefore, in addition to providing a method for augmenting non-neural tissues, the present invention also provides a method for augmenting the central nervous system of a mammal by administering MNSC progeny to a site or sites outside the CNS.

Whether the MNSC progeny have augmented a particular tissue can be ascertained by labeling the MNSC progeny prior to transplantation and looking for the presence of the label in the tissue of interest. For example, X-Gal histochemistry is used to detect cells that have been genetically modified to express β-galactosidase prior to transplantation. Lund-Hansen et al., *Histochem.* 81(4): 321–330 (1984). Fluorescent or luminescent markers can be also be used, such as green fluorescent protein (GFP). Chalfie et al., *Science* 263:802–805 (1994). Certain luminescent markers described in U.S. Pat. No. 5,650,135, can be used and subsequently detected using non-invasive measures. BrdU labeling can also be used but may not be preferred as the label dilutes as the cells divide. Microspheres, and any other type of label suitable for tracking cells can be used. Non-autologous transplanted cells may be detectable without prior labeling, for example, by detecting the presence of foreign major histocompatibility complex (MHC) molecules or other identifying antigens that may be present on the cell surface once the cells have differentiated.

MNSCs may be induced to proliferate ex vivo and the progeny transplanted in the undifferentiated state without further modification or manipulation ex vivo, as the stem cell progeny automatically repopulate the lost or malfunctioning cell type in response to intrinsic environmental signals. Methods for generating large numbers of enriched populations of MNSCs for transplantation purposes are disclosed in U.S. Pat. No. 5,750,376. As used herein, the phrase "enriched population of multipotent neural stem cells" means a population of cells that contains a higher percentage of MNSCs than are present in the tissue from which the MNSCs originated. Typically, less than about 0.1% of cells obtained from mammalian neural tissue are MNSCs. Therefore, an enriched population of MNSCs that contains about 1% MNSCs typically contains at least 10 times more MNSCs than that present in the neural tissue from which the MNSCs are derived. Secondary and subsequent MNSC cultures prepared according to the methods disclosed in the patent and publications referenced above, generally provide a suitably enriched population of MNSCs. When undifferentiated MNSC progeny are used for augmenting a selected tissue, the enriched population of MNSCs, preferably comprises at least 1% MNSCs. More preferably, at least about 5% of the cells will be MNSCs. Still more preferred is the use of enriched population of MNSCs comprising at least 10% MNSCs. It is possible to obtain enriched populations of MNSCs comprising at least about 20% MNSCs. The use of highly enriched populations of MNSCs, containing at least 15%, or in some cases 20%, MNSCs may be desirable in that it may reduce the total number of cells needed for transplantation.

The percentage of MNSCs present in a culture can be estimated by passaging a known number of cells from the culture to fresh culture medium containing one or more growth factors that induces multipotent neural stem cell proliferation, such as epidermal growth factor (EGF) and fibroblast growth factor (FGF). The percentage of cells that form neurospheres indicates the approximate percentage of stem cells present in the culture. The term "neurosphere" refers to a cluster of precursor cells that forms when a MNSC is induced to proliferate in vitro. A neurosphere comprises the progeny of a single MNSC which includes daughter MNSCs and undifferentiated progenitor cells. U.S. Pat. No. 5,750,376 describes neurospheres in detail and provides photographs of neurospheres. Cell sorting techniques could be used to further enrich the cultures for MNSCs, by separating committed progenitor cells from MNSCs.

Once an enriched population of MNSCs is obtained, the cells may be transplanted in the undifferentiated state without further modification or manipulation in vitro, as the neural stem cells automatically repopulate lost or malfunctioning cell types in response to intrinsic environmental signals.

Alternatively, undifferentiated MNSC progeny may be pretreated prior to transplantation, with one or more factors, such as cytokines, growth factors, or other signals that increase the efficiency of the cells to produce progeny that differentiate into a specific cell type. Examples of differentiation-inducing factors that can be used in MNSC progeny include members of the fibroblast growth factor family (FGFs 1–9); neurotrophins such as brain-derived neurotrophic factor (BDNF), glial-derived neurotrophic factor (GDNF), NT-3, NT-4/5; interleukins (IL-1 to IL-18); stem cell factors; erythropoietin; colony stimulating factors such as macrophage colony stimulating factor (MCSF) and granulocyte-macrophage colony stimulating factor (GMCSF); hepatocyte growth factor (HGF); insulin and insulin-like growth factors (e.g. IGF-1 & IGF-2); members of the transforming growth factor beta (TGF-$\beta$) including basic myelin proteins (BMP-2, BMP-4, BMP-5, BMP-6, BMP-7), activins A & B, decapentaplegic (dpp), 60A, OP-2, dorsalin, GDFs (1, 3, and 9), GDNF, nodal, MIS, inhibin-$\alpha$, and transforming growth factors betas (TGF-$\beta$1, TGF-$\beta$2, TGF-$\beta$3, TGF-$\beta$5); vitamin and vitamin derivatives such as retinoic acid, and vitamin D; hormones such as progesterone, estrogen, adrenocorticotrophic hormone (ACTH), thyrotropic-releasing hormone (TRH), luteinizing hormone releasing hormone (TRH); neurotransmitters; peptides such as substance P, vasoactive intestinal peptide (VIP), carnosine, cholecystokinin (CCK) and CCK-like peptide; endorphins and enkephalins; solubilized proteoglycans (e.g. heparan); members of the eph family; prostaglandins; amino acids such as gamma-aminobutyric acid (GABA), glycine, glutamate, cysteine, taurine and aspartate; serum; and cell-conditioned culture medium.

As an alternative to transplanting undifferentiated MNSC progeny, the cells can be either in the process of differentiating or have differentiated ex vivo into specific cell types before transplantation by placing the cells in an environment that induces the stem cells to produce progeny that differentiate into the desired lineage. Depending on the desired phenotype, neural stem cell progeny can be induced to differentiate along a particular lineage by modification of the culture environment for example, by the addition of one or more growth factor or cytokines, and/or coculture of the neural stem cell progeny with cells from selected cell lines or feeder cells that provide a substratum and/or release extrinsic factors into the culture medium that influence the differentiative pathway of the MNSC progeny. In addition, manipulation of the substrate on which the cells are grown can influence the phenotypic outcome of a population of cells, either prior to transplantation or once transplanted. Current culture techniques can be used to influence the differentiative pathway of the MNSC progeny. For example, culture conditions known to influence the differentiative fate of the progeny of early embryonic blastula stem cells can be used. (see Keller, supra). Thus, ex vivo techniques can be used to provide a population of cells for transplantation that is enriched for the presence of newly generated, undifferentiated or selectively differentiated progeny of the neural stem cells.

MNSC progeny that have been cultured ex vivo can be subjected to "xenoincubation" prior to transplantation. Xenoincubation involves an initial transplantation of the MNSC progeny into a host animal such as a monkey, or pig to induce differentiation of the MNSC progeny. For example, neural tissue is removed from a patient requiring tissue or organ transplantation (e.g. blood, kidney, liver, skin, pancreas etc). Alternatively, the neural tissue is obtained from an allogeneic donor. MNSCs from the neural tissue are proliferated ex vivo using known proliferation methods to produce MNSC progeny which are then administered to a xenogeneic host, such as a monkey or pig, which will subsequently be used as an organ or tissue donor. Optionally, the organ or tissue of interest may have been compromised to increase the efficiency by which the transplanted MNSC progeny to augment the tissue, for example, by integrating with and/or appropriately differentiating into cells of the tissue or organ. After the donor organ or tissue of interest has been sufficiently augmented by the transplanted MNSC progeny, it is harvested and transplanted into the recipient using procedures known in the art. This method can be used to reduce the risk of rejection of transplants from xenogeneic donors, because allogeneic or autologous cells are incorporated with the organ or tissue of interest. This method can also be used to provide a supply of animal donors that can serve as living blood banks. These animals will have their endogenous hematopoietic systems destroyed or compromised and then reconstituted with human cells. This provides an immediately available source of fresh human blood for transfusion purposes.

In addition to the above possible ex vivo modifications, MNSC progeny can also be genetically modified so that upon transplantation, they produce a desired expression product, for example, one that alleviates the symptoms of a specific disorder. The genetically modified cells could contain a desired gene, such as a gene capable of expressing a missing peptide, a disease-resistant protein or other beneficial protein. In contrast to the other stem cell systems, such as the hematopoietic stem cell system, methods are known which allow MNSCs to be induced to continuously divide under appropriate ex vivo culture conditions, making them excellent targets for genetic modification. MNSC progeny can also be genetically modified to "knock-out" or remove undesired genes. The term "genetic modification" as used herein refers to the stable or transient alteration of the genotype of a precursor cell by intentional introduction of exogenous DNA, or by knocking-out or otherwise altering existing genes. Exogenous DNA that is introduced may be synthetic, or naturally derived, and may contain genes, portions of genes, or other useful DNA sequences. Methods for genetic modification of cells are well-known in the art. Methods for introducing exogenous DNA into MNSC progeny are disclosed in U.S. Pat. No. 5,750,376. It may be desirable to genetically modify the MNSC progeny if they are to be used for transplantation into a patient to alleviate the present or future symptoms of a specific disease with a genetic basis. The cells can be genetically modified before transplantation using an appropriate technique such as homologous recombination. The cells are then transplanted to the desired location where they receive extrinsic signals from the surrounding environment to produce progeny that differentiate into the desired cell type.

Undifferentiated and/or differentiated neural stem cell progeny are transplanted into a patient using any suitable treatment regime known in the art. For example, the cells can be administered directly to a site requiring augmentation using an injection cannula, or other suitable delivery device. Micro- or macroencapsulated cells can be administered to sites requiring augmentation when it is not necessary for the cells to become integrated with the host tissue. The cells can also be administered systemically so that they circulate throughout the host and migrate to and incorporate with various tissues requiring augmentation. The cells can also be administered orally, peritoneally, subcutaneously, topically or by any other method that allows them to incorporate with host tissue requiring augmentation. For example, intravenous injection of pancreatic progenitor cells into diabetic baboons and beagles with diabetes related to an autoimmune disorder have had promising results (Kenyon, N. S. Emerging applications of hematopoietic stem cell transplantation in the treatment of insulin dependent diabetes, *IBC on Hematopoietic Stem Cells* (1997)). However, as noted, MNSCs automatically proliferate in vivo in response to environmental signals. Therefore, the number of MNSCs needed for transplantation may be fewer than required for traditional cell transplantation therapies. The approximate number of MNSC progeny that are needed for a particular purpose can be determined using routine experimentation, for example using animal models.

The optimum number of cells can be determined using routine clinical trials. For systemic administration of MNSC progeny, procedures presently used for the transplantation of hematopoietic stem cells for the treatment of various disorders can be followed (see Bensinger et al. *J. of. Clin. Oncology*, 13(10):2547–2555 (1995); Tricott et al., *Blood* 85(2):588–596). For systemic administration of MNSC progeny, approximately $10^2$ to $10^7$, and more typically, about $10^3$ to $10^6$ neural precursor cells/kg body weight should be sufficient. In many instances, transplanted MNSCs continue to proliferate in vivo in appropriate response to extrinsic signals to produce the necessary amount of new cells to augment a particular tissue. Tumor formation of transplanted MNSC progeny has not been observed. It is believed that this is because transplanted neural stem cells respond appropriately to environmental cues and cease proliferation after the treated tissue has been sufficiently augmented.

Xenogeneic and allogeneic transplantation using MNSCs and stem cell progeny can be carried out without transplant rejection. For example, no signs of transplant rejection were observed in studies where the hematopoietic system of mice were severely depleted and reconstituted using human MNSC progeny. This could be due to a reduced level of or missing MHC molecules on the surface of MNSCs. MHC molecules have been found to be absent from the surface of mouse MNSCs, and may be absent from the surface of MNSCs of other species as well. (see Motluk, A., *New Scientist*. p. 40 (1998)). In any event, because MNSCs can be obtained from all mammals, and proliferated ex vivo to achieve suitable numbers of cells for transplantation, in most cases autologous or allogeneic transplantation will probably be preferred. When the transplantation is not for the treatment of a genetic disorder that also affects MNSCs, the use of autologous cells may be most preferred. However, certain genetic defects may be correctable by genetic modification of a patient's MNSCs ex vivo and transplantation of the cells back into the patient.

When undifferentiated neural stem cell progeny are transplanted, they may, in response to environmental signals, subsequently differentiate into cells normally found in the tissue that is being augmented. For example, undifferentiated MNSC progeny, when injected systemically into a mammal with a depleted hematopoietic system, generate new blood cells. As another example, MNSC progeny, when injected into a myelin-deficient CNS, generate oligodendrocytes which form the needed myelin (See Hammang et al., supra; U.S. application Ser. No. 08/479,796). Neural stem cell progeny can also augment tissue while remaining in the undifferentiated state. For example, undifferentiated neural stem cell progeny that have been genetically modified to secrete a needed biological factor may be administered to a tissue in need of that biological factor. Undifferentiated neural stem cell progeny can also augment tissue simply by serving as a reserve source of new cells. As existing cells in the tissue die or become non-functional, as a result of injury, disease, apoptosis, or aging, the undifferentiated neural stem cell progeny, in response to environment signals, generate new cells to replenish injured, dead, or non-functional cells.

MNSC progeny transplantation can be used to augment normal, healthy tissues, or any tissue in need of augmentation as a result of disease, disorder, injury or aging. Injuries such as wounds, muscle or ligament tears, weakened heart muscle due to myocardial infarction, and burns can benefit from MNSC transplantation. For example, MNSC progeny can be administered directly to a wound, where, in response to the surrounding environment, they differentiate into fibroblast and other appropriate cell types. Alternatively, the MNSC progeny can be administered away from the site of injury, and the cells migrate to the area(s) in need of cell replenishment.

MNSC progeny can also be administered to a patient at risk for a certain disease or condition, or after the onset of the disease or condition. For example, MNSC progeny can be administered before or immediately after a myocardial infarction. Death is more likely to occur after a myocardial infarction, not during, due to the cellular death that occurs in the heart wall after the ischemic event. When these cells die, the heart is weakened and may rupture if it beats too strongly. Until fibroblasts fill in the lesion with scar tissue (~10 days), the patient is most susceptible to dying as the result of a ruptured heart wall. MNSC progeny administered systemically or directly to, or nearby, the heart muscle prior to or immediately after the myocardial infarction episode, incorporate with the heart muscle and differentiate into appropriate cell types, thereby speeding up the healing process and reducing the likelihood of complications occurring after the myocardial infarction.

MNSC progeny can also be administered to aging tissue to provide structural support, serve as a reserve to replace aging or dying cells, and/or provide other augmentation functions. Newly generated neural stem cell progeny can also be transplanted prophylactically into a recipient to provide an order of protection from anticipated senescence-related, naturally-occurring conditions.

Additionally, the neural stem cell progeny can be used for the prevention or treatment of other naturally-occurring disorders for example bone injuries, as well as disorders that occur more commonly with age, such as osteoporosis, and stress fractures. Administration of MNSC progeny may prevent or treat other bone disorders as well.

MNSC progeny can also be used to augment normal tissue. For instance, it may be desired for body builders or laborers to have neural stem cell progeny differentiate into new muscle tissue to add additional tissue size and muscle strength. It may also be desirable to differentiate MNSC progeny into fat tissue to be used to enlarge specific parts of the body or increase body weight. Similar approaches are useful for developing supra-normal efficacy in all normal tissues.

In addition to the above transplantation uses of MNSC progeny, differentiating or differentiated MNSC progeny that have been subjected to ex vivo environments that induce MNSC progeny to differentiate into non-neural cell types can be used to generate large quantities of cells of a variety of neural and non-neural phenotypes. The different cell types can be used for drug-screening, preparation of cDNA libraries, and as models for discovering mechanisms of tissue development.

All cited references, including patents and patent applications, are incorporated herein by reference in their entireties.

The following examples are for illustrative purposes only and are not to be construed as limiting the scope of the invention in any manner.

EXAMPLE 1

Figure 1B:
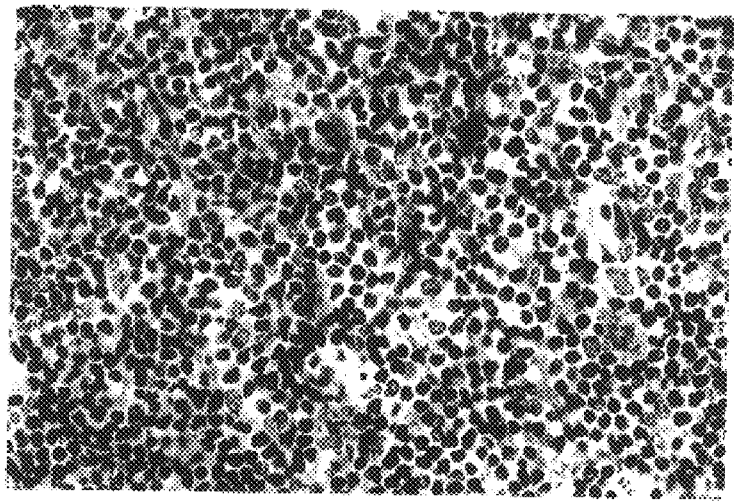
Figure 1C:
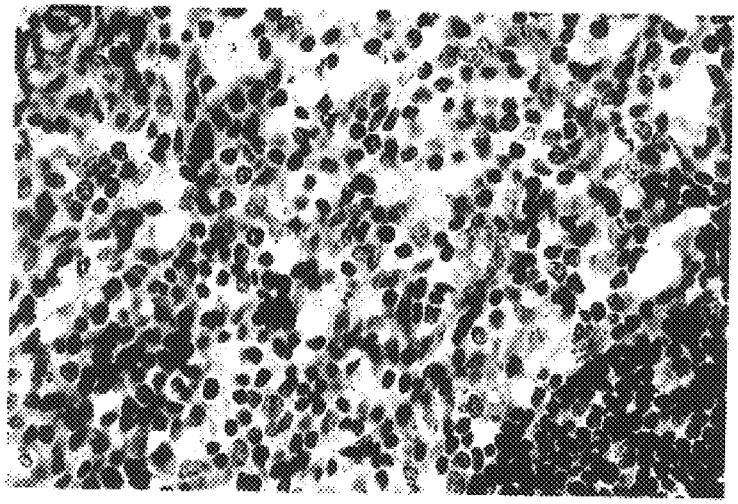
Figure 1D:
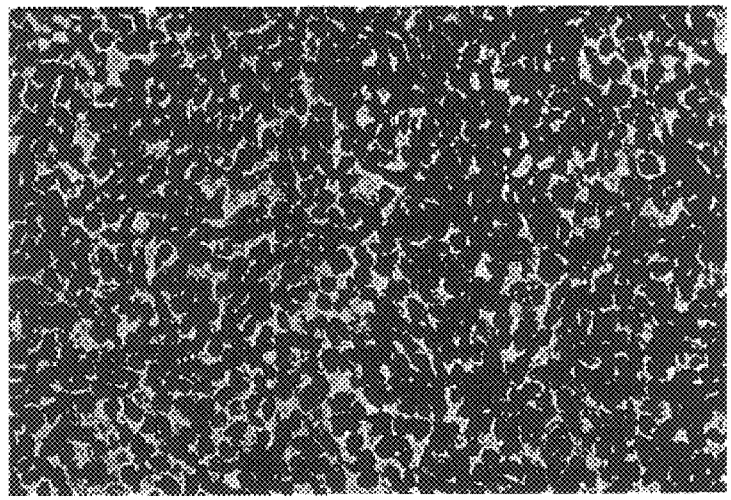
FIGS. 1D–1F show tissue sections (10 µm) of mouse thymus which were assayed for the presence of β-gal (Mag. 63×). EBSS negative and ROSA positive controls are shown in FIGS. 1D and 1E, respectively.
Figure 1E:
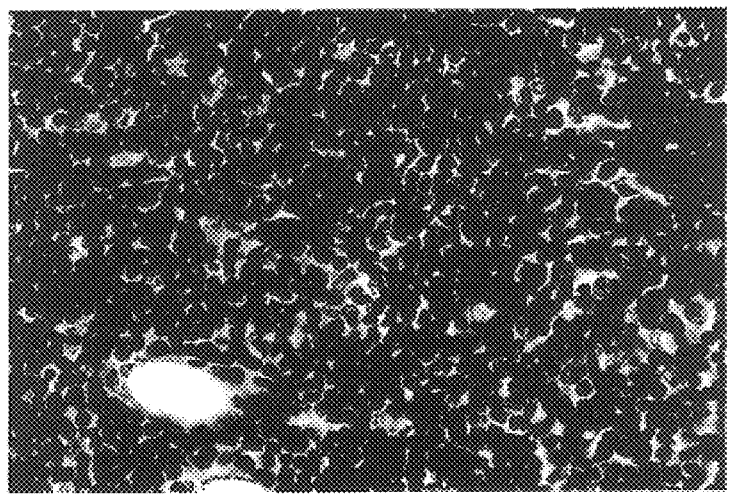
Figure 1F:
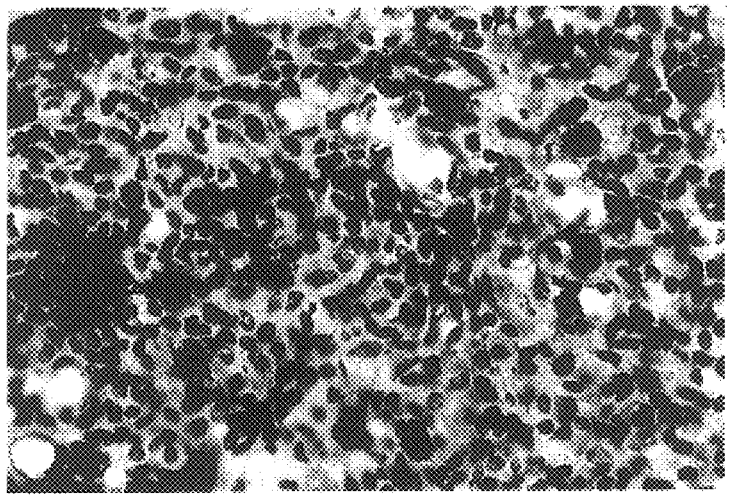
Figure 2A:
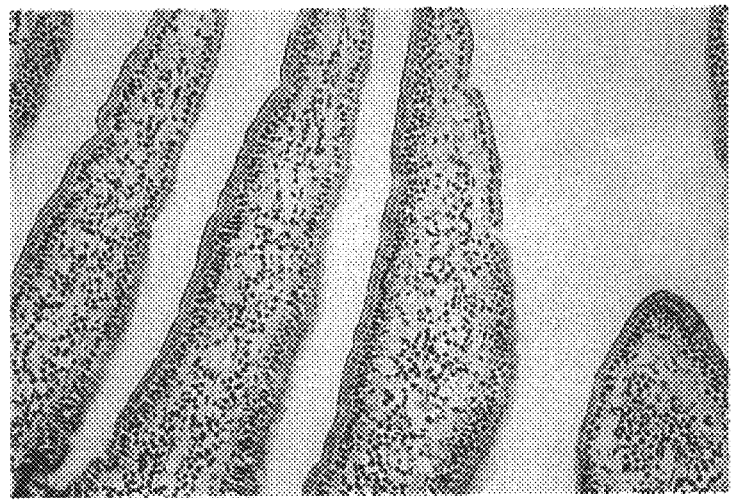
FIGS. 2A–2C show tissue sections (10 µm) of mice small intestine which were assayed for the presence of β-gal.
Figure 2B:
Figure 2C:
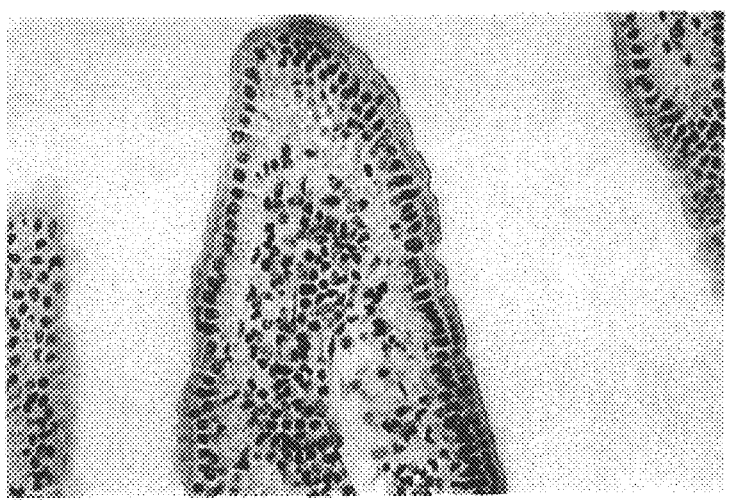
Figure 2D:
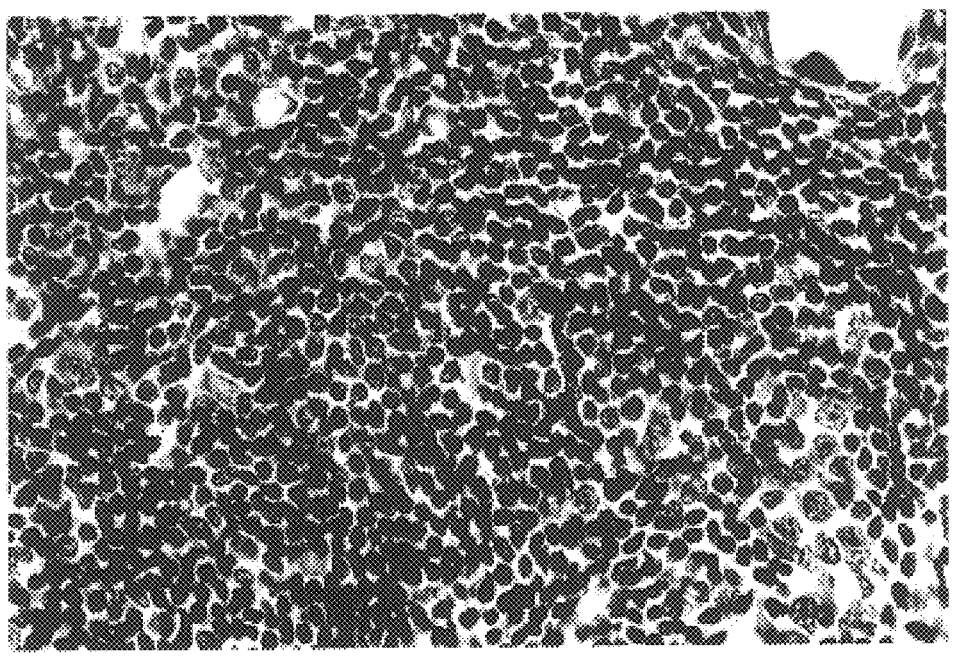
FIGS. 2D and 2E show sections (10 µm) of mouse lymphatic tissue which were assayed for the presence of β-gal (Mag. 63×). An EBSS negative control is shown in FIG. 2D.
Figure 2E:
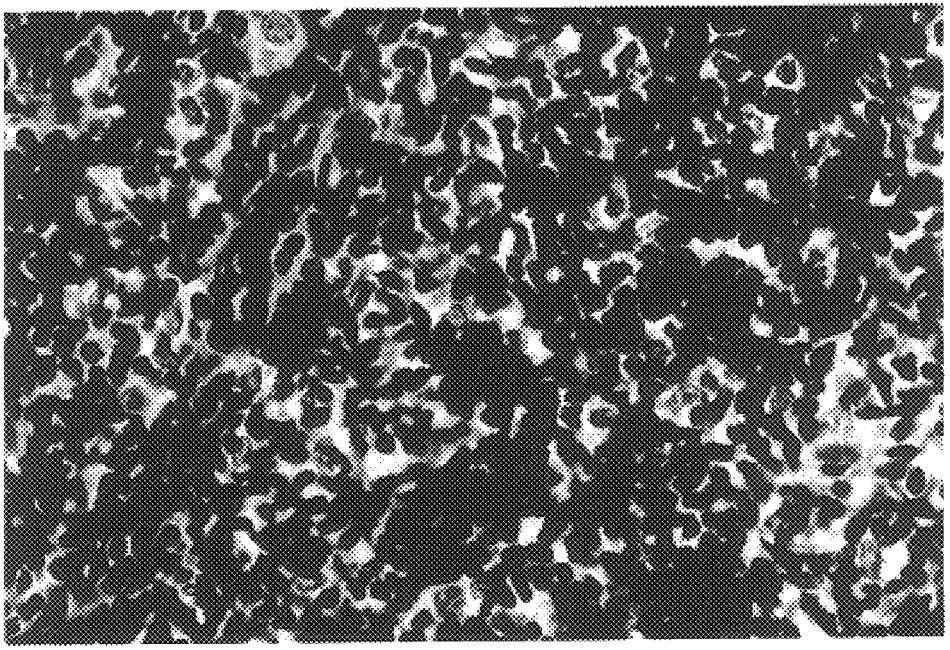
Figure 3A:
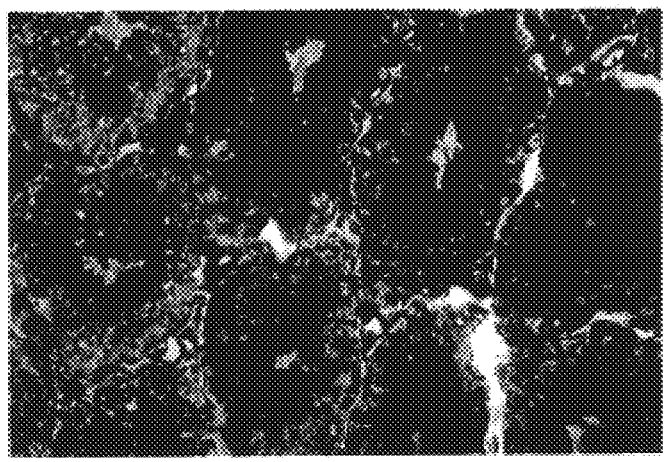
FIGS. 3A–3D show tissue sections (10 µm) of mouse testes which were assayed for the presence of β-gal. ROSA positive and EBSS negative controls are shown in FIGS. 3A and 3B, respectively (Mag. 20×).
Figure 3B:
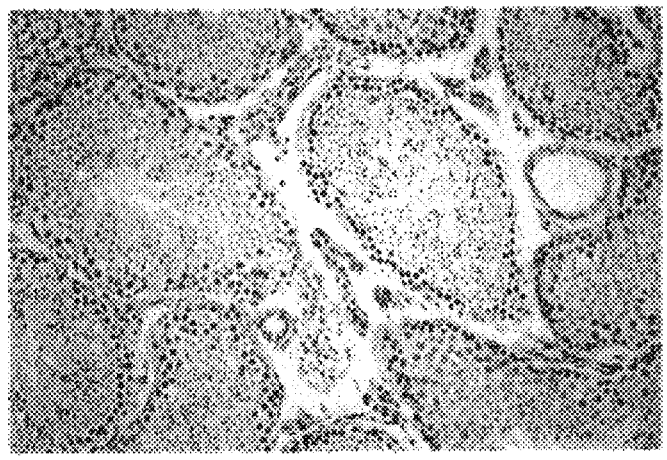
Figure 3C:
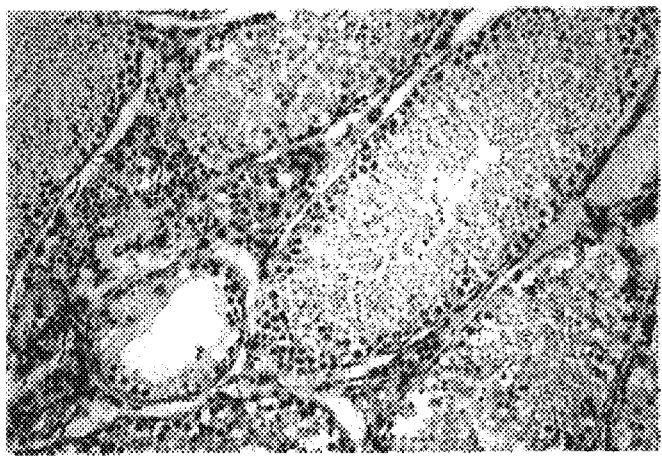
Figure 3D:
Figure 3E:
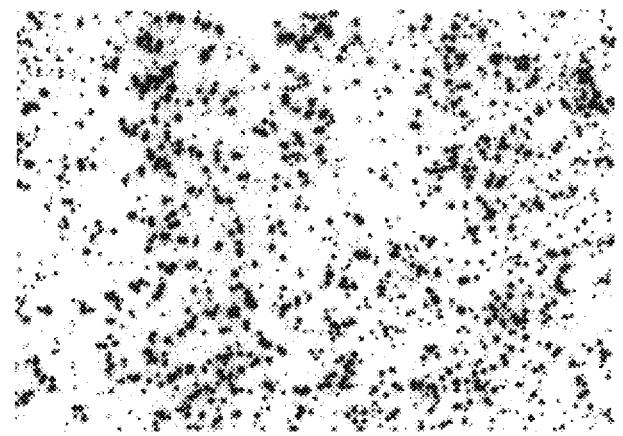
FIGS. 3E–3H show tissue sections (10 µm) of mouse central nervous tissue (brain) which were assayed for the presence of β-gal. ROSA positive and EBSS negative controls are shown in FIGS. 3E and 3F, respectively.
Figure 3F:
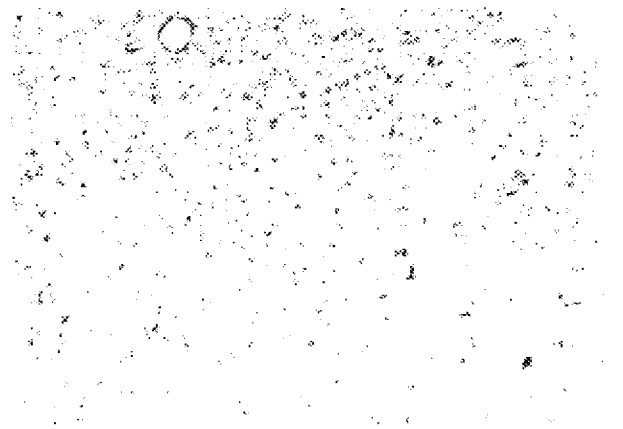
Figure 3G:
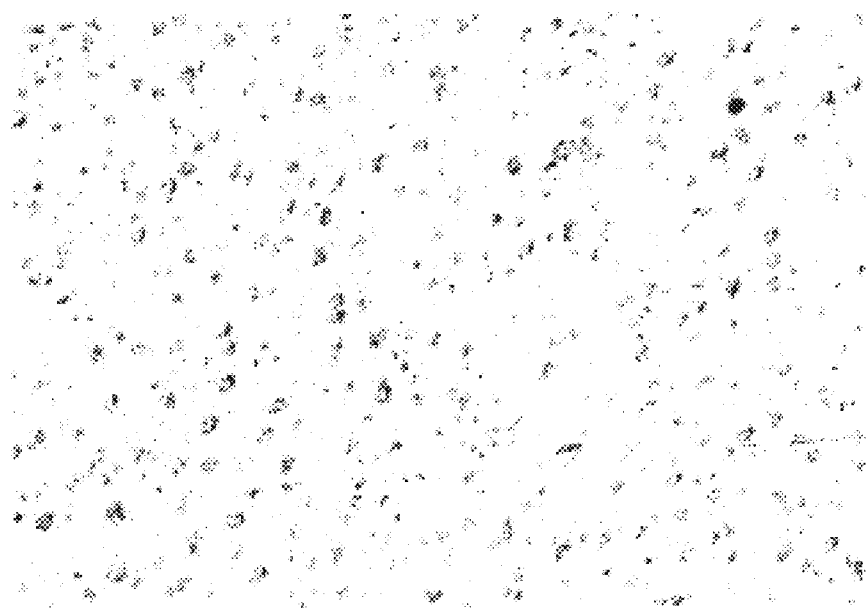
Figure 3H:
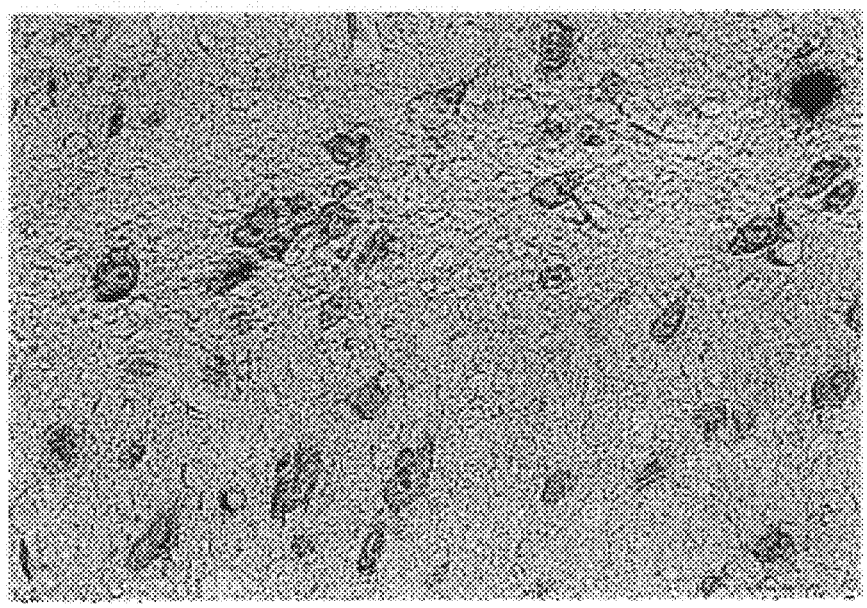

U.S. application Ser. No. 09/100,679, now U.S. Pat. No. 6,093,531, entitled "Generation of Hematopoietic Cells from Multipotent Neural Stem Cells, which was filed on Jun. 19, 1998, and which is a continuation-in-part of U.S. application Ser. No. 60/060,289, describes experiments that show that systemic administration of β-gal labeled MNSC progeny will give rise to complete reconstitution of all major hematolymphatic lineages in animals that have had their hematopoietic systems severely compromised by radiation. The majority of animals treated with embryonic mouse, embryonic human, or adult mouse MNSC progeny survived prolonged periods (6–15 months). In contrast, the majority of negative control animals, irradiated mice that received systemic administration of saline, died within one month. Further X-Gal histochemical analysis, used to detect β-galactosidase activity, was used on the animals that received the MNSCs and revealed the presence of donor cells incorporated into ectodermally-derived tissue (the grain), mesoderm-derived tissue (gonads (testes), lymph nodes, spleen, and heart) and endodermally-derived tissue (small intestines and thymus). Thus, MNSCs which have been systemically administered to mammals will migrate to and augment tissues originating from all 3 embryonic germ layers. The results of these studies are shown in the FIGS. 1A through 4J.

EXAMPLE 2

In vivo Generation of Non-neural Differentiated Cells from MNSCs-Skeletal Muscle Muscle damage is chemically induced in either a tibialis anterior, gastrocnemius or soleus muscle of each of a number of anaesthetized mice by administering 25 μl of 1 mM cardiotoxin (Latoxan) in 0.9% saline into the muscle, essentially as described in Ferrari et al., supra.

β-gal labeled MNSC progeny, obtained from embryonic or adult ROSA mouse neural tissue or embryonic human neural tissue, using the methods outlined in US. Pat. No. 5,750,376, are administered into the damaged muscle sites essentially as described in Ferrari et al., supra, or administered systemically by tail vein injections to the experimental animals as outlined in U.S. application Ser. No. 09/100,679, now U.S. Pat. No. 6,093,531, filed Jun. 19, 1998, which is a continuation of U.S. application Ser. No. 60/060,289. The stem cell progeny are administered to individual animals at different time intervals during the necrotic period following the cardiotoxic insult.

The injured muscles and contralateral control muscles are examined at various times after injection (5 days to 5 weeks). Whole mount histochemical staining of the injured muscles which received mouse cells reveal fibers containing β-gal$^+$, centrally aligned nuclei occupying the injury site. Similarly, the appropriate detection methods (see Ferrari, et al., supra) reveal the presence of human neural stem cell-derived muscle fibers in the lesioned region of animals which received human embryonic neural stem cell progeny.

EXAMPLE 3

Systemic Administration of MNSC to Augment CNS Tissue

The 6-OHDA lesion rat model of Parkinson's disease is used to measure the effects of systemic administration of labeled MNSC progeny on rotation behavior. MNSC progeny, are prepared and administered into the tail vein of the 6-OHDA lesioned rat using the methods referenced in Example 2. The ability of systemically administered MNSC progeny to augment the lesioned areas of the brain and overcome the rotational bias produced by the unilateral 6-OHDA lesions is observed using histochemical and behavioral analysis.

EXAMPLE 4

In vitro Generation of Non-neural Differentiated Cells from MNSCs

A. Cardiac Muscle

Cardiac muscle is generated ex vivo from MNSC progeny using the culture methods described by Wobus et al. *Differentiation* 48:173–182 (1991).

B. Lymphohematopoietic cells

The method of Nakana, et al. (*Science* 265:1098–1101 (1994)) is used to generate lymphohematopoietic cells from MNSC progeny. The undifferentiated neural stem cell progeny are cocultured with OP9 stromal cell line (the cells of which lack the ability to produce functional macrophage colony stimulating factor). Neutrophils, macrophages, erythroid cells, mast cells, megakaryocytes and lymphoid cells are obtained.

The newly generated cells produced by the methods described in Examples 4A and 4B are used for transplantation, preparation of cDNA libraries, drug screening, and other purposes.

What is claimed is:

1. A method of increasing hematopoietic cells of a mammal comprising administering multipotent neural stem cell progeny at a site or sites outside said mammal's central nervous system, wherein said multipotent neural stem cell progeny integrate with said hematopoietic tissue and wherein said multipotent neural stem cell progeny are allogeneic or autologous to said mammal.

* * * * *